US010463394B2

(12) United States Patent
Hamamoto et al.

(10) Patent No.: US 10,463,394 B2
(45) Date of Patent: Nov. 5, 2019

(54) MEDICAL DEVICE

(71) Applicants: Sharp Kabushiki Kaisha, Sakai-shi, Osaka (JP); Public University Corporation Hiroshima City University, Hiroshima-shi, Hiroshima (JP)

(72) Inventors: Masaki Hamamoto, Sakai (JP); Kazuhiro Taniguchi, Hiroshima (JP); Masazumi Okajima, Hiroshima (JP)

(73) Assignees: SHARP KABUSHIKI KAISHA, Sakai (JP); PUBLIC UNIVERSITY CORPORATION HIROSHIMA CITY UNIVERSITY, Hiroshima (JP)

( * ) Notice: Subject to any disclaimer, the term of this patent is extended or adjusted under 35 U.S.C. 154(b) by 300 days.

(21) Appl. No.: 15/118,274

(22) PCT Filed: Nov. 17, 2014

(86) PCT No.: PCT/JP2014/080292
§ 371 (c)(1),
(2) Date: Aug. 11, 2016

(87) PCT Pub. No.: WO2015/125358
PCT Pub. Date: Aug. 27, 2015

(65) Prior Publication Data
US 2016/0361087 A1    Dec. 15, 2016

(30) Foreign Application Priority Data
Feb. 18, 2014    (JP) .................................. 2014-028887

(51) Int. Cl.
*A61B 17/34*    (2006.01)
*A61B 1/00*    (2006.01)
(Continued)

(52) U.S. Cl.
CPC ............ *A61B 17/34* (2013.01); *A61B 1/0016* (2013.01); *A61B 1/00147* (2013.01);
(Continued)

(58) Field of Classification Search
CPC ............ A61B 1/00147; A61B 1/00154; A61B 1/0016; A61B 17/34; A61B 2034/301;
(Continued)

(56) References Cited

U.S. PATENT DOCUMENTS 4,019,073 A * 4/1977 Vishnevsky ........ H01L 41/0913
310/322
5,105,117 A * 4/1992 Yamaguchi ............ H02N 2/004
310/323.16
(Continued)

FOREIGN PATENT DOCUMENTS

JP    02-311184 A    12/1990
JP    5-337127 A     12/1993
(Continued)

OTHER PUBLICATIONS

Hamamoto et al., "Actuator", U.S. Appl. No. 15/573,518, filed Nov. 13, 2017.
(Continued)

*Primary Examiner* — Timothy J Neal
*Assistant Examiner* — Aaron B Fairchild
(74) *Attorney, Agent, or Firm* — Keating & Bennett, LLP

(57) ABSTRACT

There is provided a medical device whose occupied space is reduced. According to an aspect of the present invention, a medical device (1) adjusts a position of a medical instrument including a rod-like insertion unit (201) for being inserted into a body. The medical device includes an ultrasonic actuator that holds the insertion unit of the medical instrument, and that displaces or rotates the insertion unit with respect to the ultrasonic actuator, and an actuator fixing unit
(Continued)

(101 and 102) that fixes a position of the ultrasonic actuator to a surgical site.

15 Claims, 13 Drawing Sheets

(51) Int. Cl.
    *A61B 17/00*       (2006.01)
    *A61B 34/30*       (2016.01)
    *H02N 2/10*        (2006.01)

(52) U.S. Cl.
CPC ...... *A61B 1/00154* (2013.01); *A61B 1/00032* (2013.01); *A61B 17/3403* (2013.01); *A61B 34/30* (2016.02); *A61B 2017/00402* (2013.01); *A61B 2017/00544* (2013.01); *A61B 2017/347* (2013.01); *A61B 2017/3409* (2013.01); *H02N 2/103* (2013.01)

(58) Field of Classification Search
CPC .... A61B 2017/00402; A61B 2017/348; A61B 2017/3484; A61B 2017/349; A61B 17/3439; A61B 2090/571; A61B 90/37; A61B 1/00108; A61B 1/00064; A61B 1/00133; A61B 2017/00398
See application file for complete search history.

(56) References Cited

U.S. PATENT DOCUMENTS

| | | | |
|---|---|---|---|
| 6,554,765 B1* | 4/2003 | Yarush | A61B 1/00039 348/73 |
| 2003/0178915 A1* | 9/2003 | Yoon | H02N 2/0025 310/323.01 |
| 2003/0208187 A1 | 11/2003 | Layer | |
| 2003/0208207 A1 | 11/2003 | Layer | |
| 2004/0027032 A1 | 2/2004 | Moteki et al. | |
| 2005/0234293 A1* | 10/2005 | Yamamoto | A61B 1/00082 600/102 |
| 2005/0234435 A1 | 10/2005 | Layer | |
| 2007/0236106 A1 | 10/2007 | Koc et al. | |
| 2007/0277815 A1* | 12/2007 | Ravikumar | A61B 90/57 128/99.1 |
| 2008/0103358 A1 | 5/2008 | Suzuki | |
| 2009/0039806 A1* | 2/2009 | Kudo | H02N 2/004 318/116 |
| 2009/0261690 A1 | 10/2009 | Mashimo et al. | |
| 2009/0278421 A1 | 11/2009 | Hamamoto et al. | |
| 2010/0022825 A1* | 1/2010 | Yoshie | A61B 1/00133 600/104 |
| 2011/0208000 A1* | 8/2011 | Honda | A61B 1/00016 600/118 |
| 2011/0245844 A1 | 10/2011 | Jinno | |
| 2012/0228994 A1* | 9/2012 | Wischnewskiy | H01L 41/0986 310/317 |
| 2016/0351786 A1 | 12/2016 | Hamamoto | |

FOREIGN PATENT DOCUMENTS

| | | |
|---|---|---|
| JP | 09-056667 A | 3/1997 |
| JP | 09-140663 A | 6/1997 |
| JP | 2000-157485 A | 6/2000 |
| JP | 2005-524440 A | 8/2005 |
| JP | 2005-270171 A | 10/2005 |
| JP | 2005-328697 A | 11/2005 |
| JP | 2007-275885 A | 10/2007 |
| JP | 2008-283756 A | 11/2008 |
| JP | 2009-018044 A | 1/2009 |
| JP | 2009-153283 A | 7/2009 |
| JP | 2009-278702 A | 11/2009 |
| JP | 2011-206312 A | 10/2011 |
| JP | 2013-183563 A | 9/2013 |
| WO | 2008/038817 A1 | 4/2008 |
| WO | 2015/125359 A1 | 8/2015 |

OTHER PUBLICATIONS

Hamamoto, "Friction Drive Actuator", U.S. Appl. No. 15/110,117, filed Jul. 7, 2016.
Hamamoto et al., "Ultrasonic Actuator", U.S. Appl. No. 15/574,974, filed Nov. 17, 2017.
Ariyama et al., "Catheter Insertion Module Using Friction Wheel Mechanism for Vascular Surgery", Journal of the Japan Society of Computer Aided Surgery, vol. 15, No. 2, 2013, pp. 162-163.
Official Communicatioin issued in International Patent Application No. PCT/JP2014/080292, dated Feb. 24, 2015.

\* cited by examiner

MEDICAL DEVICE

TECHNICAL FIELD

The present invention relates to a medical device.

BACKGROUND ART

In a celoscope surgery (laparoscopic surgery or thoracoscopic surgery), a surgical procedure is performed in such a way that an endoscope (for example, a rigid endoscope) and a manipulator (or forceps) are inserted after make a few small holes into a patient's abdomen while an operator observes an image displayed on a monitor of the endoscope. This celoscope surgery does not need laparotomy. Accordingly, a patient is less burdened, and it is possible to considerably reduce the number of days required until the patient is recovered after surgery or is discharged from a hospital. Therefore, it is expected that an application field of the celoscope surgery is enlarged.

On the other hand, in the celoscope surgery, it is necessary to insert multiple medical instruments into the patient's body through an opening punctured on the patient's body surface. Therefore, for example, persons or the medical instruments extracorporeally come into contact with and interrupted by each other, thereby causing a problem in that forceps and an endoscopic camera come into contact with each other and imposing significant restrictions on an operation of a medical device.

For example, in order to solve the above-described problem, PTL 1 discloses a medical robot system which can avoid mutual interference between arms for moving the respective medical instruments while visibility suitable for a user is ensured.

CITATION LIST

Patent Literature

PTL 1: Japanese Unexamined Patent Application Publication No. 2011-206312 (Published on Oct. 20, 2011)

SUMMARY OF INVENTION

Technical Problem

However, although the medical robot system disclosed in PTL 1 can avoid mutual interference between the arms, the overall system for using a surgical robot increases in size and becomes expensive. In a robot arm, a position of the manipulator inside a patient's body functions as a fixed point. Accordingly, a movable range of the robot arm increases inevitably outside the patient's body. Therefore, it is difficult to secure a space which allows an operator to perform smooth medical treatment in the vicinity of the patient.

The present invention is made in view of the above-described problem, and an object thereof is to provide a medical device whose occupied space is reduced.

Solution to Problem

According to an aspect of the present invention, in order to solve the above-described problem, there is provided a medical device which adjusts a position of a medical instrument provided with a rod-shaped insertion unit for inserting the medical instrument into a body. The medical device includes an actuator that holds the insertion unit of the medical instrument, and that displaces or rotates the insertion unit to the actuator, and an actuator fixing unit that fixes a position of the actuator to a surgical site. The actuator holds the insertion unit at respective contact points on a plurality of housings connected so as to be openable and closeable and having restoring force applying in a direction where the plurality of housings are closed together.

Advantageous Effects of Invention

According to the aspect of the present invention, it is possible to provide a medical device whose occupied space is reduced.

DESCRIPTION OF EMBODIMENTS

Embodiment 1

Overview of Medical Device

Figure 1:
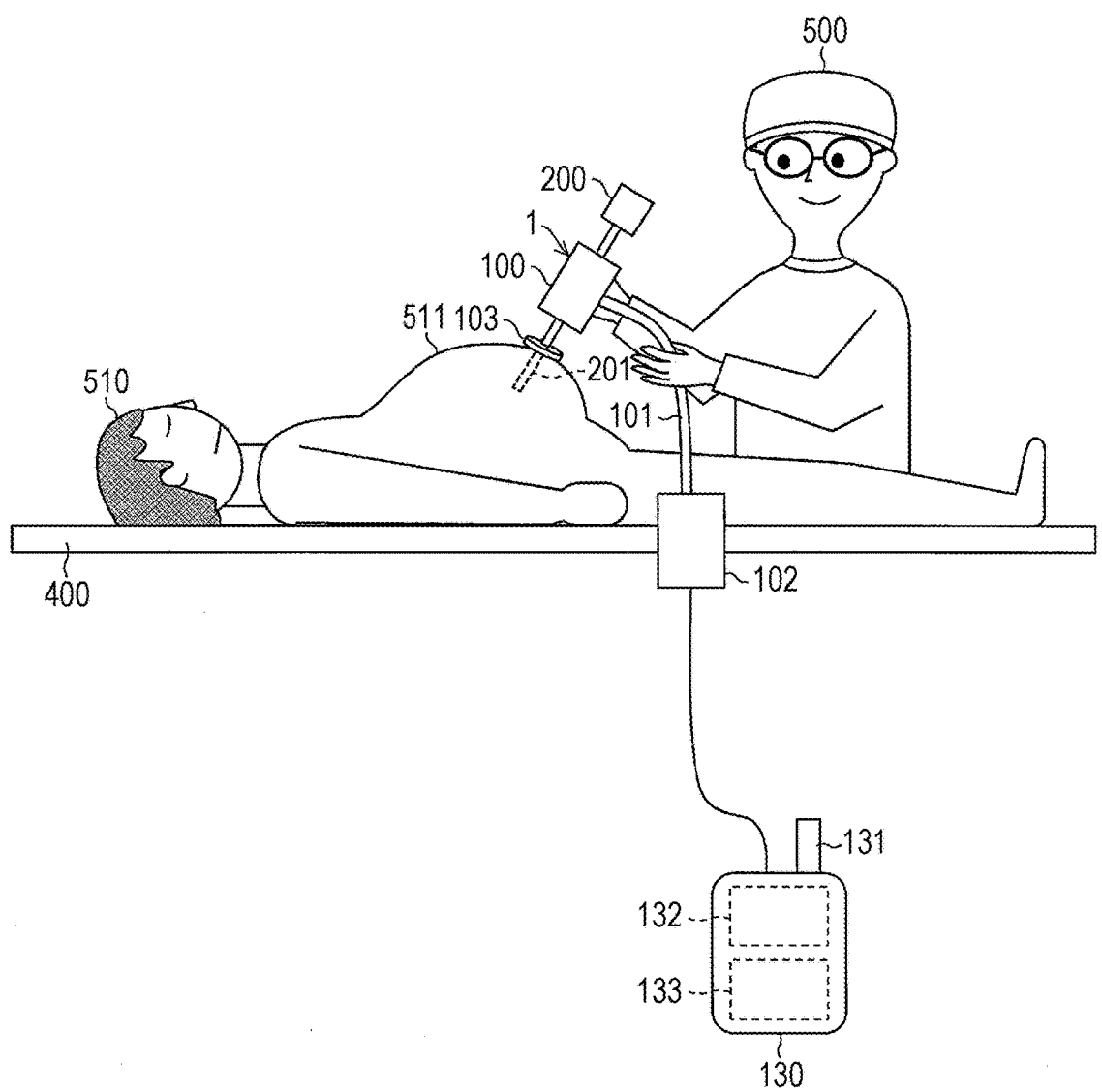
FIG. 1 is a schematic diagram illustrating a schematic configuration of a medical device according to an embodiment of the present invention.

FIG. 1 is a schematic diagram illustrating a schematic configuration of a medical device 1 according to an embodiment of the present invention. In the present embodiment, as an example to which the present invention is applicable, a situation is assumed where an insertion unit (sheath tube) 201 of a rigid endoscope 200 is inserted into an abdominal cavity of an abdomen 511 of a patient 510 lying on an operating table 400 so that a surgeon 500 performs treatment based on an image obtained therefrom.

In FIG. 1, the medical device 1 includes an insertion unit conveyance unit 100, a flexible arm (actuator fixing unit) 101, a stand (actuator fixing unit) 102, a surgical port 103, a controller unit (control device) 130, and the rigid endoscope 200. Details of the insertion unit conveyance unit 100 and the controller unit 130 will be described later. The medical device 1 adjusts a position of the rigid endoscope 200.

In the flexible arm 101, the insertion unit conveyance unit 100 is fixed to and supported by one end thereof. The flexible arm 101 can be bent by a hand so as to have a desired shape. That is, the insertion unit conveyance unit 100 is arranged at and fixed to a desired position of the surgeon 500 by using the flexible arm 101.

The stand 102 fixes the other end of the flexible arm 101, thereby fixing the flexible arm 101 to a side of the patient 510 lying on the operating table 400. The stand 102 is installed in (fixed to) the operating table 400.

The surgical port 103 is a medical instrument having a through-hole for inserting a medical instrument into an abdominal cavity of the patient 510, and is arranged on a surface of the abdomen 511 of the patient 510. The surgical port 103 is not indispensably used depending on an operative procedure, and is not an indispensable configuration element in the present embodiment.

In the present embodiment, the rigid endoscope 200 having a cylindrical (rod-like) insertion unit 201 is used as an example of the medical instrument, but a configuration is not limited thereto. Instead of the rigid endoscope 200, it is possible to use a medical instrument having a rod-like (columnar) insertion unit for inserting the medical instrument into a body of the patient 510. For example, those which have a surgical instrument such as forceps disposed in a distal end of the columnar insertion unit or a columnar catheter serving as the insertion unit can be used as the medical instrument.

(Configuration of Insertion Unit Conveyance Unit)

Figure 2:
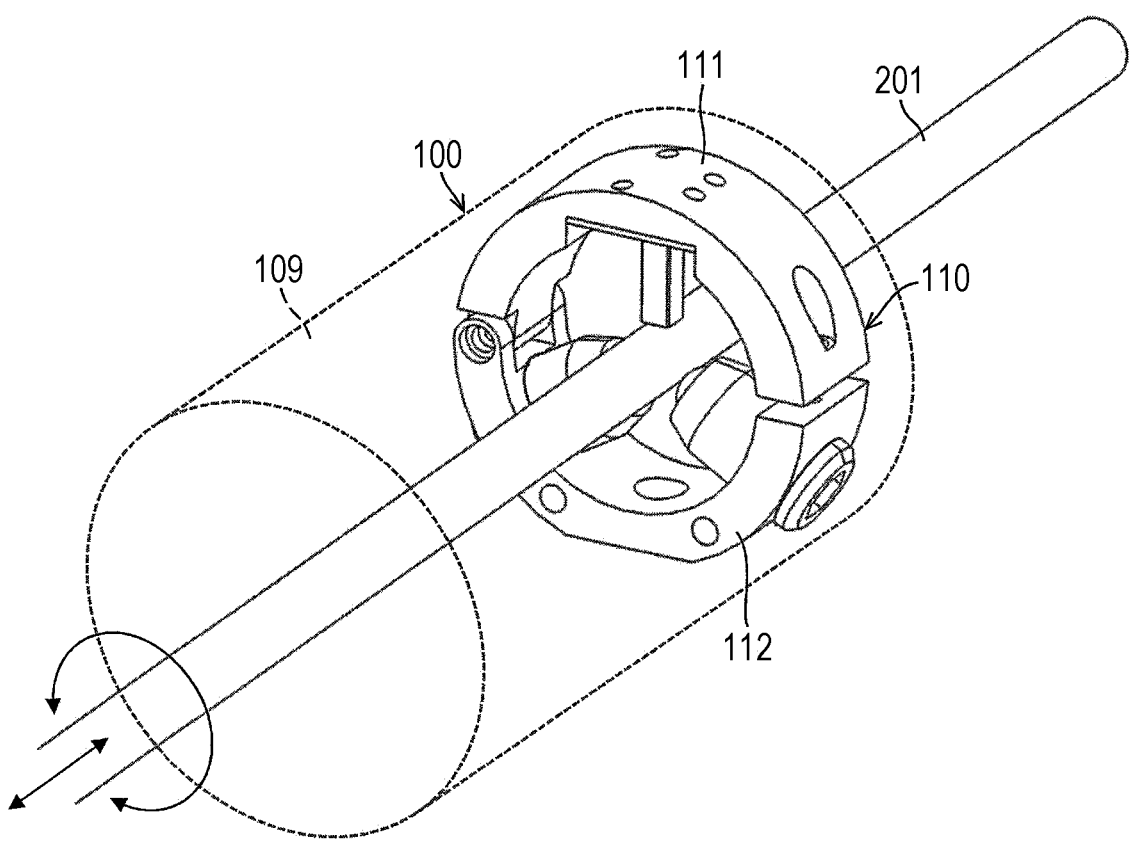
FIG. 2 is a perspective view illustrating a schematic configuration of an insertion unit conveyance unit of the medical device.

FIG. 2 is a perspective view illustrating a schematic configuration of the insertion unit conveyance unit 100. As illustrated in FIG. 2, the insertion unit conveyance unit 100 includes an actuator holding unit (actuator fixing unit) 109 and an ultrasonic actuator (actuator, friction drive actuator) 110.

The actuator holding unit 109 is a hollow housing which holds the ultrasonic actuator 110, and an end of the flexible arm 101 is fixed to a side surface of the actuator holding unit 109. The actuator holding unit 109, the flexible arm 101, and the stand 102 configure an actuator fixing unit for fixing the ultrasonic actuator 110 to the vicinity of a surgical site.

Figure 3:
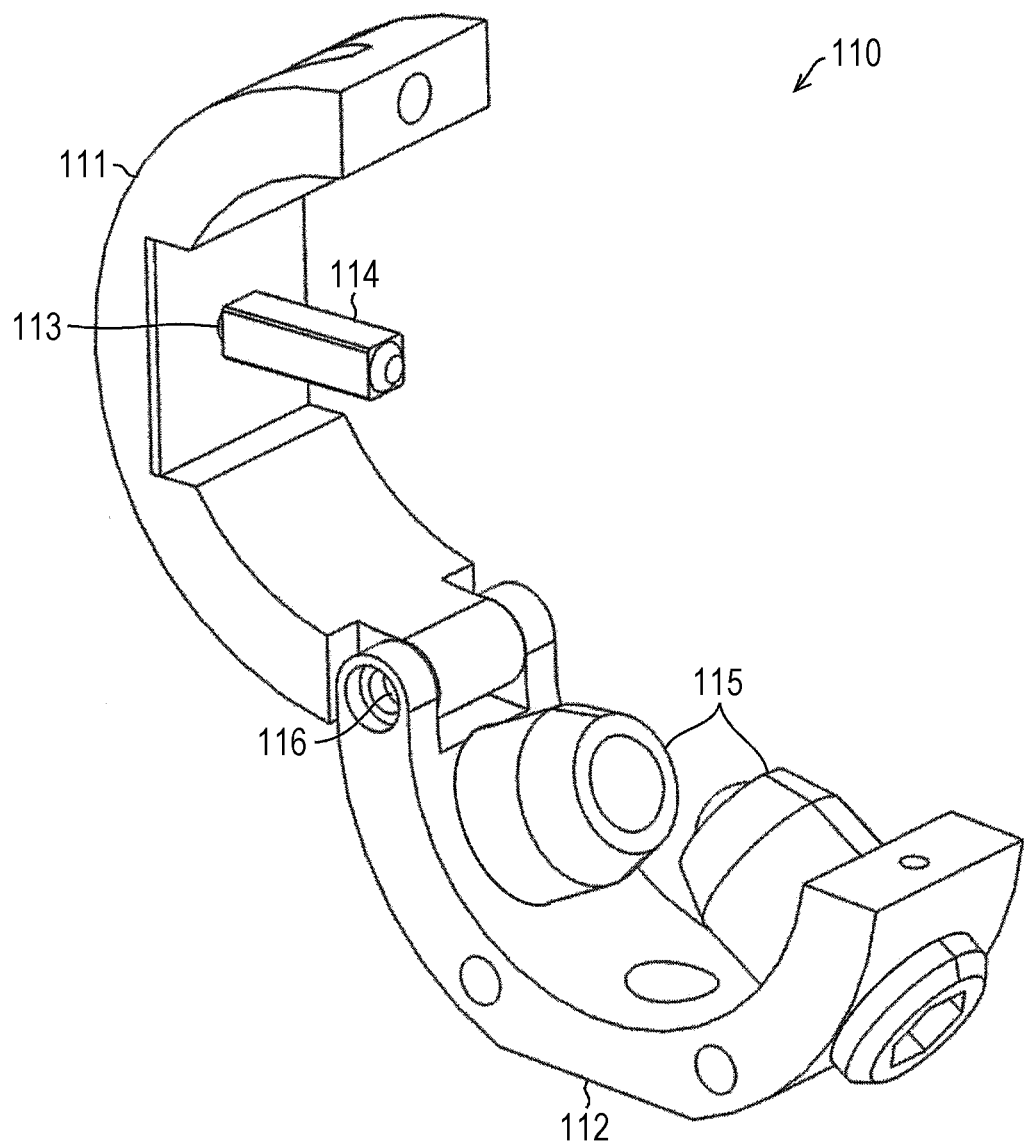
FIG. 3 is a perspective view illustrating a schematic configuration of an ultrasonic actuator of the medical device.

FIG. 3 is a perspective view illustrating a schematic configuration of the ultrasonic actuator 110. As illustrated in FIG. 3, the ultrasonic actuator 110 includes a housing 111, a housing 112, a stay 113 disposed on an inner surface of the housing 111, an ultrasonic vibrator (friction drive element) 114 fixed to the housing 111 via the stay 113, and two ball bearings (sliding bodies) 115 fixed to an inner surface of the housing 112. The housing 111 and the housing 112 are connected so as to be openable and closeable. The ultrasonic actuator 110 conveys the insertion unit 201 of the rigid endoscope 200 to the vicinity of the surgical site in a state where the actuator holding unit 109 fixes a position for the surgical site of a body lumen.

The housing 111 and the housing 112 have a restoring force applied in a direction where both of these are closed together by a preloading spring (restoring member) 116. When the housing 111 and the housing 112 are closed together, both of these configure an annular housing. When the housing 111 and the housing 112 are closed together, the restoring force of the preloading spring 116 presses the ultrasonic vibrator 114 and the two ball bearings 115 against a side surface of the insertion unit 201. That is, the rigid endoscope 200 is held in a direction perpendicular to an axial direction of the insertion unit 201 by the ultrasonic vibrator 114 and the two ball bearings 115 (refer to FIG. 2). When the housing 111 and the housing 112 are opened away from each other, the ultrasonic vibrator 114 and the ball bearing 115 are moved away from each other. Accordingly, the insertion unit 201 is released from the ultrasonic vibrator 114.

Here, the two ball bearings 115 respectively come into point contact with a side surface of the rigid endoscope 200. Therefore, if elastic deformation is considered in each contact portion of a projection 45 and the two ball bearings 115, in order to hold the rigid endoscope 200, it is necessary to dispose at least two restricting locations in a direction perpendicular to the axial direction of the insertion unit 201. For example, it is conceivable to hold another location of the rigid endoscope 200 by newly disposing three ball bearings 115 on an inner surface of the actuator holding unit 109. Here, in order to facilitate the description, the three ball bearings disposed on the inner surface of the actuator holding unit 109 are not illustrated.

(Configuration of Ultrasonic Vibrator)

Figure 4:
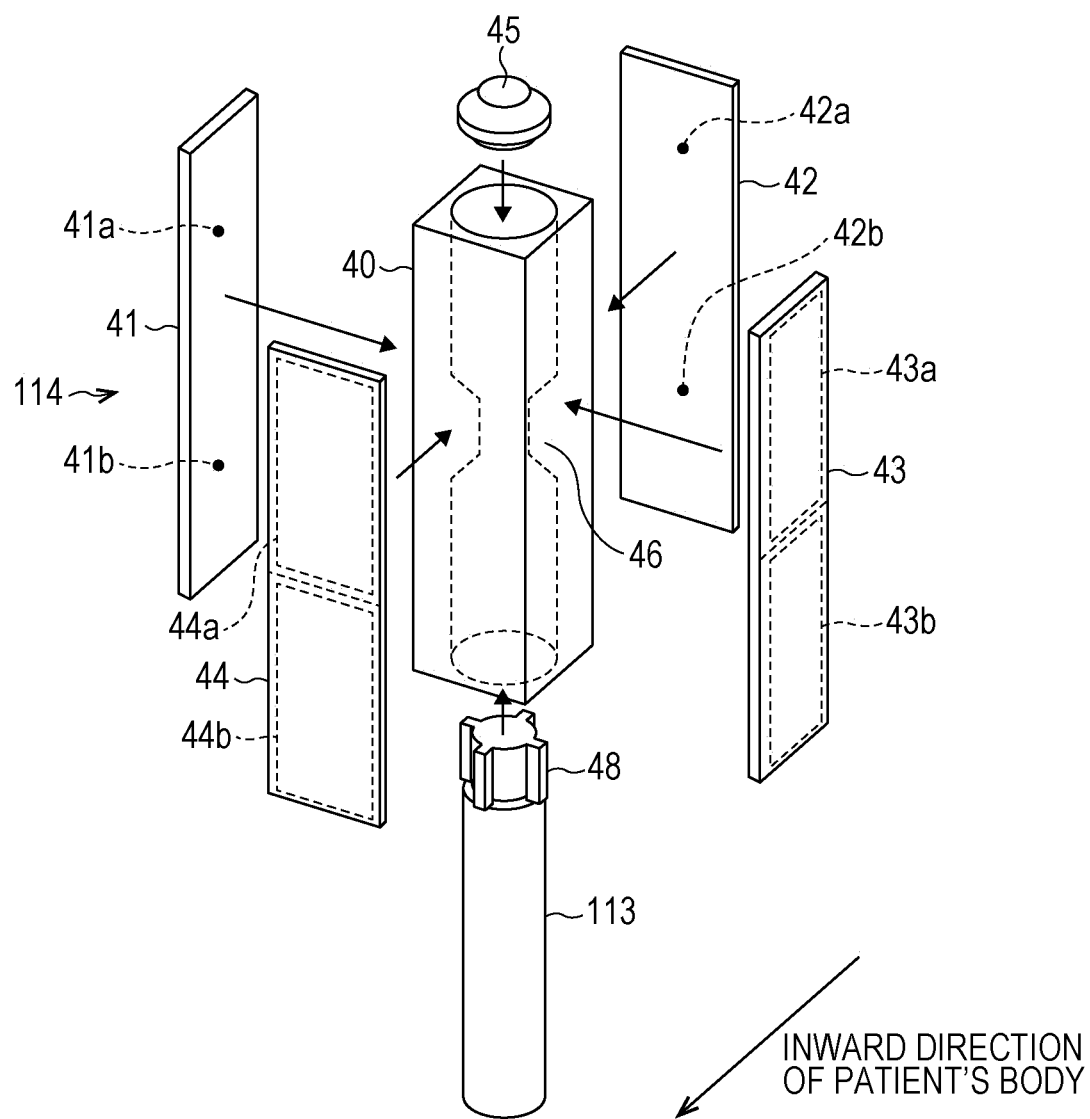
FIG. 4 is a perspective view illustrating a schematic configuration of an ultrasonic vibrator of the ultrasonic actuator.

FIG. 4 is a perspective view illustrating a schematic configuration of the ultrasonic vibrator 114. As illustrated in FIG. 4, the ultrasonic vibrator 114 includes the stay 113, a vibrator 40, the projection 45, piezoelectric elements 41 to 44, upper electrodes 41a to 44a, and lower electrodes 41b to 44b.

The stay (holding unit) 113 is a rod-like member, and a distal portion thereof has a key 48 for preventing the rotation of the ultrasonic vibrator 114.

The vibrator 40 is a hollow prism made of stainless steel, and a cross-sectional shape thereof is a substantially square shape. The hollow portion (cavity) extends along an axis of the columnar vibrator 40, and penetrates the vibrator 40. A narrow portion 46 is formed on an inner surface of the vibrator 40 which defines the hollow portion. The inner surface of the vibrator 40 defines a first cavity and a second cavity whose diameter is narrower than that of the first cavity.

The narrow portion 46 defines the second cavity in the vibrator 40. A key groove having a shape corresponding to the distal portion of the stay 113 is disposed in the narrow portion 46 in order to prevent the rotation of the vibrator 40. The key 48 is fitted to the key groove, thereby fixing the vibrator 40 to the housing 111 via the stay 113. The fitting portion (narrow portion 46) is located at a position corresponding to a node of two vibrations (to be described later, standing wave vibrations). Accordingly, the fitting portion does not hinder the vibrations.

In the present embodiment, the narrow portion 46 is disposed in the vicinity of the center of the hollow portion of the vibrator 40. However, the narrow portion 46 may be disposed at any position where the vibrator 40 can be fixed to the housing 111, and a configuration is not limited thereto.

The projection 45 is a truncated cone-shaped member disposed on a distal surface of the vibrator 40, and an end surface thereof comes into line contact with the side surface of the insertion unit 201. Here, as an example, the projection 45 is a brass-made product in which a diameter of a truncated cone bottom surface is 1.8 mm, a diameter of an upper surface is 0.8 mm, and a truncated cone height is 0.5 mm. However, a shape and a material of the projection 45 are not limited to the above-described configuration. The end surface of the projection 45 may be a convex surface, and the projection 45 and the insertion unit 201 may be brought into point contact with each other.

The distal end of the columnar vibrator 40 is pressed against the side surface of the columnar insertion unit 201 (operation element) via the projection 45. The axis of the columnar vibrator 40 (longitudinal direction) and the axis of the columnar insertion unit 201 (longitudinal direction) are orthogonal to each other. The distal end of the vibrator 40 may be directly brought into contact with the insertion unit 201 by omitting the projection 45.

The piezoelectric elements 41 to 44 are plate-like elements having a property of generating a stress change if a voltage is applied thereto, and are installed on (fixed to) each side surface of the vibrator 40. A material of the piezoelectric elements 41 to 44 is ceramic or crystal.

The upper electrodes 41a to 44a and the lower electrodes 41b to 44b are installed on (fixed to) a surface opposite to the surface where the piezoelectric elements 41 to 44 are installed in the vibrator 40. The planar upper electrodes 41a to 44a are disposed so as to cover an upper half (projection 45 side from the narrow portion 46) of the piezoelectric elements 41 to 44. The planar lower electrodes 41b to 44b are disposed so as to cover a lower half of the piezoelectric elements 41 to 44. The upper electrode and the lower electrode which are disposed in one piezoelectric element are arranged parallel to each other along the axis of the vibrator 40 (longitudinal direction). The upper electrode and the lower electrode which are disposed in one piezoelectric element are separated so that both of these are not electrically connected to each other.

A voltage is supplied to the electrode (the upper electrodes 41a to 44a or the lower electrodes 41b to 44b), thereby expanding and contracting a portion corresponding to the electrode in the piezoelectric elements 41 to 44. In this manner, the piezoelectric elements 41 to 44 are vibrated. For example, in one piezoelectric element 41, a portion corresponding to the upper electrode 41a and a portion corresponding to the lower electrode 41b are differently vibrated. Therefore, the upper electrode 41a and a portion corresponding to the upper electrode 41a in the piezoelectric element 41 correspond to a first vibration generation element. The lower electrode 41b and a portion corresponding to the lower electrode 41b in the piezoelectric element 41 correspond to a different second vibration generation element. The piezoelectric elements may be separated from each other so as to correspond to the upper electrode and the lower electrode.

It is desirable to perform waterproofing treatment for wiring to each electrode and the controller unit 130 (to be described later). The ultrasonic vibrator 114 is minutely deformed in a ppm level. Accordingly, it is possible to employ a general waterproof coating method.

(Configuration of Controller Unit)

As illustrated in FIG. 1, the controller unit 130 includes an instruction input unit 131, a drive signal generation unit (voltage supply unit, operation instruction unit) 132, and a battery 133 which supplies power thereto. The controller unit 130 is detachably connected to the insertion unit conveyance unit 100 by a cable passing through the stand 102 and the flexible arm 101.

The instruction input unit 131 is an input device for inputting an instruction of an operator (user), for example, an input device such as a joystick. For example, the operator manually tilts the joystick to the right and left or back and forth, thereby inputting the instruction to convey (displace or rotate) the insertion unit 201 of the rigid endoscope 200. The instruction input unit 131 outputs the input instruction of the operator to the drive signal generation unit 132. For example, the input instruction of the operator designates a moving direction and a moving speed of the insertion unit 201.

Based on the input instruction of the operator, the drive signal generation unit 132 generates a drive signal for exciting a desired vibration in the piezoelectric elements 41 to 44, and applies the drive signal to the corresponding piezoelectric element. The drive signal is an alternating voltage. The drive signal generation unit 132 determines a phase difference between two drive signals in accordance with the moving direction. The drive signal generation unit 132 determines the amplitude of the voltage of the drive signal or a duty ratio of the drive signal in accordance with the moving speed.

In a case where the input instruction of the operator indicates a forward movement or a rearward movement of the insertion unit 201, the drive signal generation unit 132 generates a drive signal to be supplied to each electrode of the piezoelectric elements 42 and 44 which oppose each other. In a case where the input instruction of the operator indicates the rotation of the insertion unit 201, the drive signal generation unit 132 generates a drive signal to be supplied to each electrode of the piezoelectric elements 41 and 43 which oppose each other.

(Conveyance Principle of Ultrasonic Vibrator)

Next, a conveyance principle of the ultrasonic vibrator 114 will be described in detain with reference to FIGS. 5 to 9. In order to facilitate the description, the projection 45 side of the ultrasonic vibrator 114 is referred to as an upper side, and the stay 113 side is referred to as a lower side.

Figure 5:
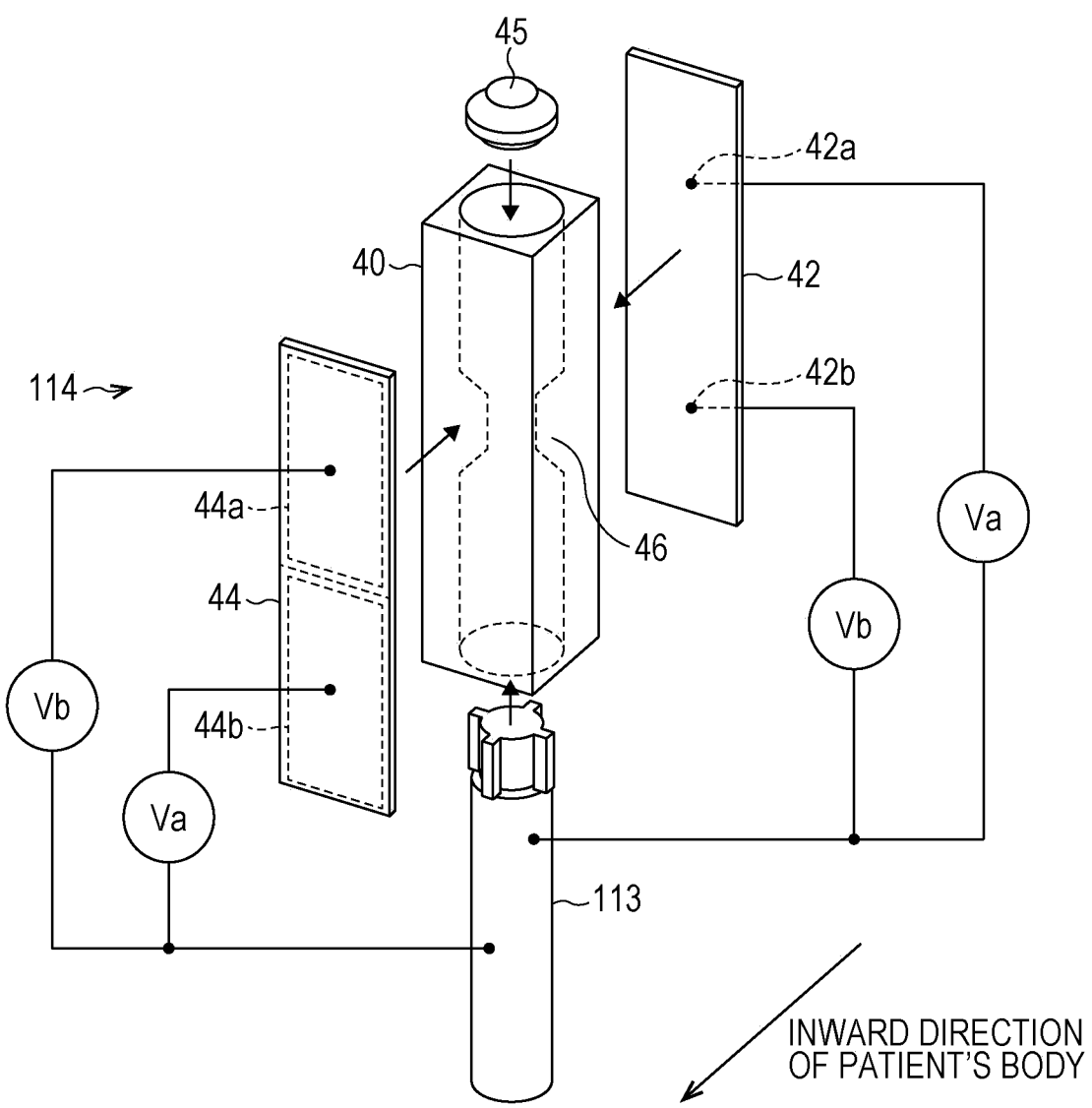
FIG. 5 is an exploded perspective view illustrating the ultrasonic vibrator and a voltage supplied thereto.

FIG. 5 is an exploded perspective view illustrating the ultrasonic vibrator 114 and a voltage supplied thereto. In FIG. 5, in order to facilitate the description, the illustration of the piezoelectric elements 41 and 43 is omitted. The drive signal generation unit 132 supplies respective alternating voltages mutually having different phase to each of two electrodes of the piezoelectric elements 41 to 44. The drive signal generation unit 132 fixes a voltage of the stay 113 to a reference voltage (here, 0 V). The stay 113, the key 48, and the vibrator 40 are conductive members, and thus, the vibrator 40 is fixed to 0 V.

A drive signal common to the lower electrode on the opposing piezoelectric element is supplied to the upper electrode on each piezoelectric element. For example, a common alternating voltage Va is supplied to the upper electrode 42a of the piezoelectric element 42 and the lower electrode 44b of the piezoelectric element 44. A portion corresponding to the upper electrode 42a of the piezoelectric element 42 is deformed (expands and contracts) in accordance with the applied voltage Va.

A common alternating voltage Vb is supplied to the lower electrode 42b of the piezoelectric element 42 and the upper electrode 44a of the piezoelectric element 44. A portion corresponding to the lower electrode 42b of the piezoelectric element 42 is deformed (expands and contracts) in accordance with the applied voltage Vb.

Figure 6:
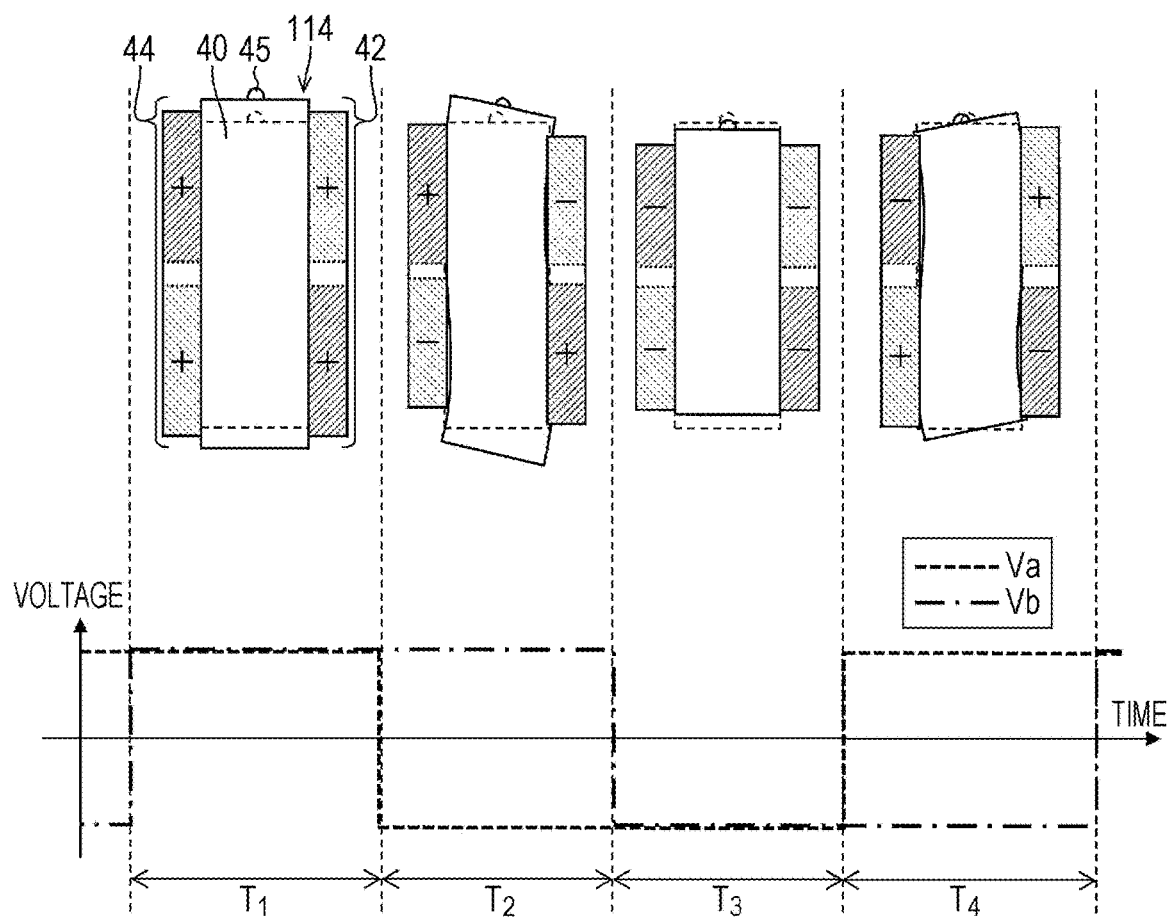
FIG. 6 is a view illustrating an alternating voltage and a time change in the ultrasonic vibrator.
Figure 7:
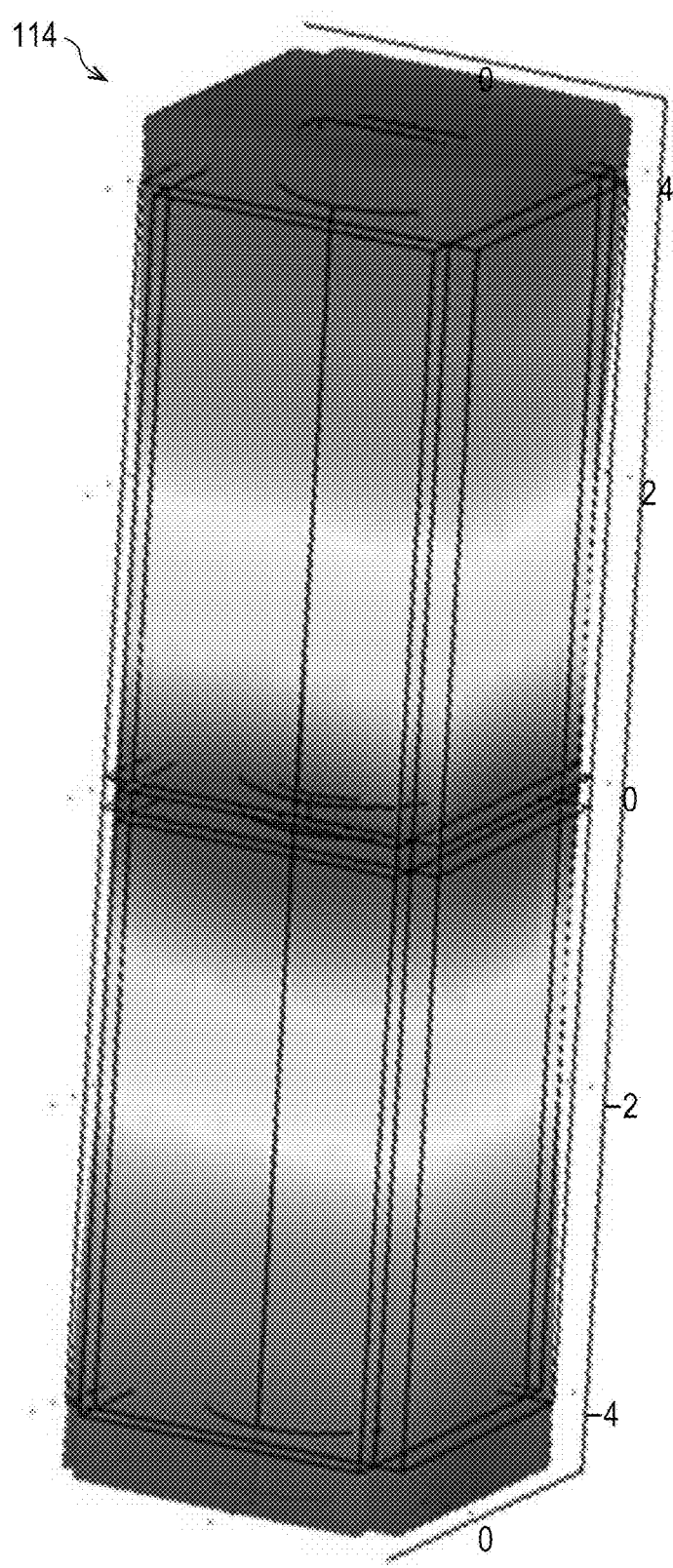
FIG. 7 is a perspective view illustrating an expanding/contracting vibration mode of the vibrator.
Figure 8:
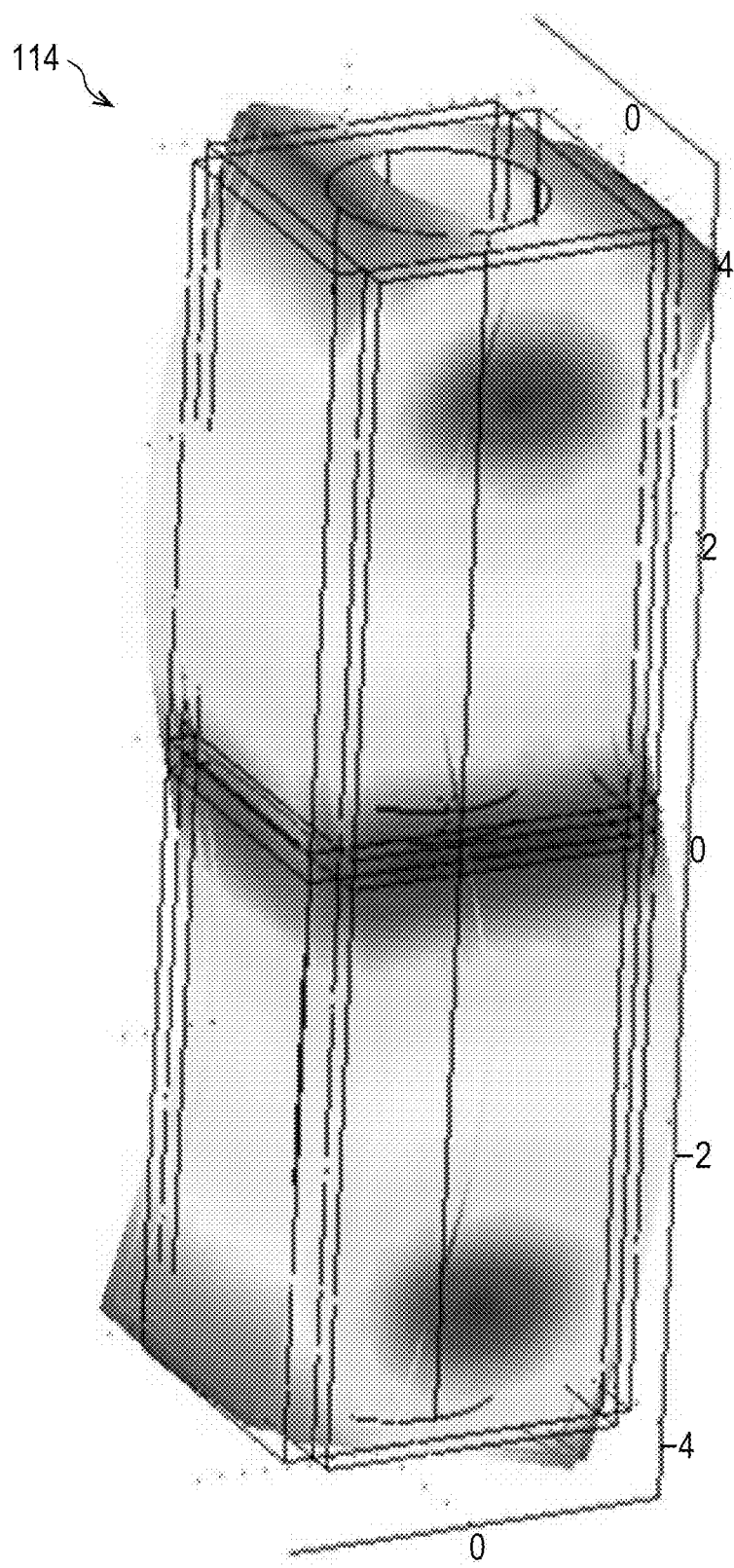
FIG. 8 is a perspective view illustrating a third bending vibration mode of the vibrator.
Figure 9:
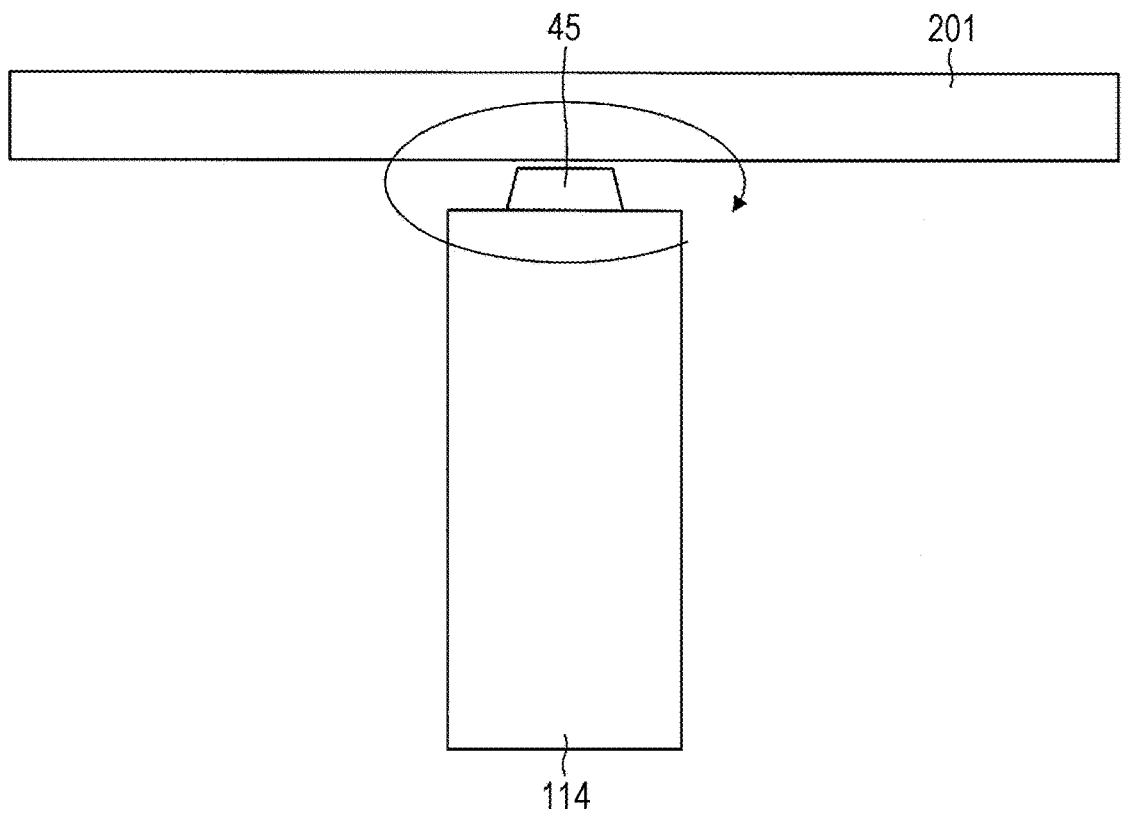
FIG. 9 is a side view illustrating a movement state of the vibrator.

FIG. 6 is a view illustrating the alternating voltages Va and Vb, and a time change in the ultrasonic vibrator 114. The upper side in FIG. 6 indicates a state of the ultrasonic vibrator 114 corresponding to respective periods of time T1 to T4. In FIG. 6, (+) and (−) of the piezoelectric elements 42 and 44 indicate portions corresponding to the electrodes to which a voltage of each polarity is applied. FIG. 7 is a perspective view illustrating an expanding/contracting vibration mode L1 of the vibrator 40. FIG. 8 is a perspective view illustrating a third bending vibration mode B3 of the vibrator 40. In FIGS. 7 and 8, a dark shade (black) portion indicates a less deformed portion in the vibrator 40, and a bright shade (white) portion indicates a much deformed portion in the vibrator 40. As illustrated in FIGS. 7 and 8, a central portion of the vibrator 40 corresponds to the node of the vibrations. FIG. 9 is a side view illustrating a movement state of the vibrator 40.

As illustrated in FIG. 6, Va and Vb are the alternating voltages of ±24 V, in which phases are different as large as 90°. When a positive polarity voltage is applied to the piezoelectric elements 42 and 44, the piezoelectric elements 42 and 44 expand in the direction along the axis of the vibrator 40 (direction to the insertion unit 201). When a negative polarity voltage is applied to the piezoelectric elements 42 and 44, the piezoelectric elements 42 and 44 contract in the direction along the axis of the vibrator 40. The piezoelectric elements 42 and 44 adhere to the vibrator 40. Accordingly, a portion corresponding to the piezoelectric elements 42 and 44 in the vibrator 40 (portion to which the piezoelectric elements adhere) expand or contract similarly. As a result, during the periods of time T1 and T3 while the two alternating voltages Va and Vb are the same polarity, the expanding/contracting vibration mode L1 (refer to FIG. 7) of the vibrator 40 is excited. During the periods of time T2 and T4 while the two alternating voltages Va and Vb are respectively different polarities, the third bending vibration mode B3 (refer to FIG. 8) of the vibrator 40 is excited. If an aspect ratio (width:height) of the square prism-shaped vibrator 40 is 1:4, the resonance frequencies of the expanding/contracting vibration mode L1 and the third bending vibration mode B3 are substantially coincident with each other.

The expanding/contracting vibration mode L1 and the third bending vibration mode B3 are excited using the same frequency, thereby deforming the vibrator 40 as illustrated in FIG. 6 during one cycle (periods of time T1 to T4). The vibration excited in each vibration mode is a standing wave vibration in which a position of the node does not vary. The narrow portion 46 of the vibrator 40 is positioned at a location corresponding to the node of the standing wave vibration (location corresponding to a portion between the upper electrode and the lower electrode).

Specifically, during the period of time T1, the vibrator 40 expands. The projection 45 is displaced (linearly moved) to the insertion unit 201 side. During the period of time T2, the vibrator 40 is bent. The projection 45 is displaced to the piezoelectric element 42 side. During the period of time T3, the vibrator 40 contracts. The projection 45 is displaced in a direction away from the insertion unit 201. During the period of time T4, the vibrator 40 is bent to a side opposite to that during the period of time T2. The projection 45 is displaced to the piezoelectric element 44 side.

As a result, as illustrated by an arrow in FIG. 9, the projection 45 arranged in the distal end of the vibrator 40 is elliptically moved. The end surface of the projection 45 is pressed against the side surface of the insertion unit 201 by the preloading spring 116. Therefore, the alternating voltages Va and Vb are applied to a set of the piezoelectric elements 42 and 44, the insertion unit 201 of the rigid endoscope 200 is conveyed along an inward direction of a patient due to friction with the projection 45. If the reference numerals of the alternating voltages Va and Vb are reversed, the insertion unit 201 is conveyed in the opposite direction. If the alternating voltages Va and Vb are applied to the piezoelectric elements 41 and 43 arranged along a circumferential direction of the axis of the insertion unit 201, the insertion unit 201 is rotated around the axis. In this way, the single ultrasonic vibrator 114 can selectively convey the insertion unit 201 in two directions (displacement (linear movement) direction and rotation direction).

The phase difference between the two alternating voltages Va and Vb determines the moving direction (rotation direction), and the amplitude (or the duty ratio) between the two alternating voltages Va and Vb determines the moving speed (rotation speed). In this way, the drive signal (alternating voltage) generated by the drive signal generation unit 132 can reflect the instruction of the operator as the operation of the rigid endoscope 200.

In the present embodiment, the two the piezoelectric elements are caused to oppose each other, thereby exciting the expanding/contracting vibration mode L1 and the third bending vibration mode B3. However, for example, the similar vibration may be excited by using only the piezoelectric elements 41 and 42. However, the present embodiment employs a good symmetrical configuration. Accordingly, unnecessary vibrations other than the expanding/contracting vibration mode L1 and the third bending vibration mode B3 are less likely to be excited. Therefore, according to the present embodiment, it is possible to improve energy efficiency.

Application Example

As an application example, the vibrator 40 employs the stainless-made hollow square prism having a square cross section whose one side is 2 mm and whose height is 8 mm. The hollow portion has a cylindrical shape whose diameter is 1.6 mm. The axis of the hollow portion and the axis of the square prism are coincident with each other. The piezoelectric elements 41 to 44 employ commercially available hardware-based PZT (PZT-5H: lead-zirconium-titanium) having a rectangular shape whose thickness is 0.2 mm, short side is 2 mm, and long side is 8 mm.

As a result, the resonance frequencies of the expanding/contracting vibration mode L1 and the third bending vibration mode B3 are all approximately 280 kHz, and are coincident with each other. In this manner, the resonance is excited in the ultrasonic vibrator 114. Therefore, it is possible to realize the conveyance (displacement and rotation) of the insertion unit 201.

Advantageous Effect the medical device 1 according to the present embodiment can cause the insertion unit 201 of the rigid endoscope 200 serving as the medical instrument to be displaced in the axial direction of the insertion unit 201 and to rotate around the axis of the insertion unit 201. The rigid endoscope 200 can view one side surface direction of the insertion unit 201. Accordingly, the rigid endoscope 200 can view any desired location inside a body lumen by using the medical device 1. In this manner, an operator (or a surgeon) van view any desired location inside the body lumen via the rigid endoscope 200.

The medical device 1 fixes the position of the ultrasonic actuator 110 by using the insertion unit conveyance unit 100 and the flexible arm 101. The insertion unit 201 of the rigid endoscope 200 is driven by the ultrasonic actuator 110 so as to be biaxial with respect to the ultrasonic actuator 110. Therefore, it is possible to minimize a space occupied by the medical device 1. Accordingly, compared to a medical robot system in the related art, the medical device 1 can secure a considerably wide working space for the surgeon 500.

For example, according to the ultrasonic actuator in the related art in which the periphery of an operation element is surrounded with a stator, a through-hole of the stator comes into contact with the entire periphery of the operation element. Thus, it is necessary to accurately machine the operation element and the stator. According to another actuator in the related art in which the operation element is conveyed using multiple rollers, in a case where dirt (blood) adheres to the operation element, there is a possibility that the friction force may be unevenly generated between the multiple rollers. The force transferred to the operation element is uneven, thereby causing a possibility of an unexpected movement.

The ultrasonic actuator 110 according to the present embodiment adopts a configuration in which the distal end (projection 45) of the single ultrasonic vibrator 114 is pressed against the side surface of the insertion unit 201 serving as the operation element in one direction. Therefore, machining tolerance can be greatly set in the ultrasonic actuator 110. Moreover, the ultrasonic actuator 110 can be easily machined and assembled. The ultrasonic vibrator 114 is pressed against the side surface of the insertion unit 201 in one direction. Accordingly, even in a case where dirt adheres to the insertion unit 201, a poor operation is less likely to occur.

Modification Example

According to the present embodiment, the actuator arranged in the vicinity of the treatment site (position of the surgical port 103) of the patient 510 drives the medical instrument (rigid endoscope 200). This reduces a space for arranging the robot arm in the related art or the endoscopic operation assistant. Each configuration element according to the present embodiment can be appropriately replaced depending on compatibility with a surgical procedure or technical progress.

For example, in the present embodiment, the actuator employs an ultrasonic motor using the ultrasonic vibrator. However, it is also possible to employ an actuator driven using air pressure or electromagnetic force.

With regard to the controller unit, the instruction input unit 131 is not limited to the joystick. For example, a semi-automatic controller can also be employed in which the operation is performed based on the position of each site calculated in accordance with an absolute position after instructing the absolute position by pointing the position on a screen.

Furthermore, if a difference in the friction force does not affect function achievement to some extent, a configuration can also be adopted in which the ball bearing 115 is replaced with a sliding body such as a fluorine resin pad. As a matter of course, the number, an arrangement, and a shape of the sliding bodies are not limited to the present embodiment as long as these do not hinder the conveyance of the insertion unit 201.

Without being limited to the square prism, the vibrator 40 may have a columnar shape having at least one side surface (plane). Multiple vibration generation elements may be disposed on one side surface so as to parallel to each other along the axis (longitudinal direction) of the columnar vibrator.

A vibration mode used as conveying force of the ultrasonic actuator, an electrode shape for exciting the vibration mode, and an applied voltage pattern can be appropriately modified depending on a type of the medical instrument to be conveyed, and are not limited to the present embodiment.

The ultrasonic actuator 110 can be used in order to convey (displace or rotate) any columnar operation element, in addition to the insertion unit of the medical instrument.

Embodiment 2

Another embodiment according to the present invention will be described as follows with reference to FIGS. 10 to 12. In order to facilitate the description, the same reference numerals will be given to members having the same function as the members described in Embodiment 1, and description thereof will be omitted.

(Outline of Medical Device)

Figure 10:
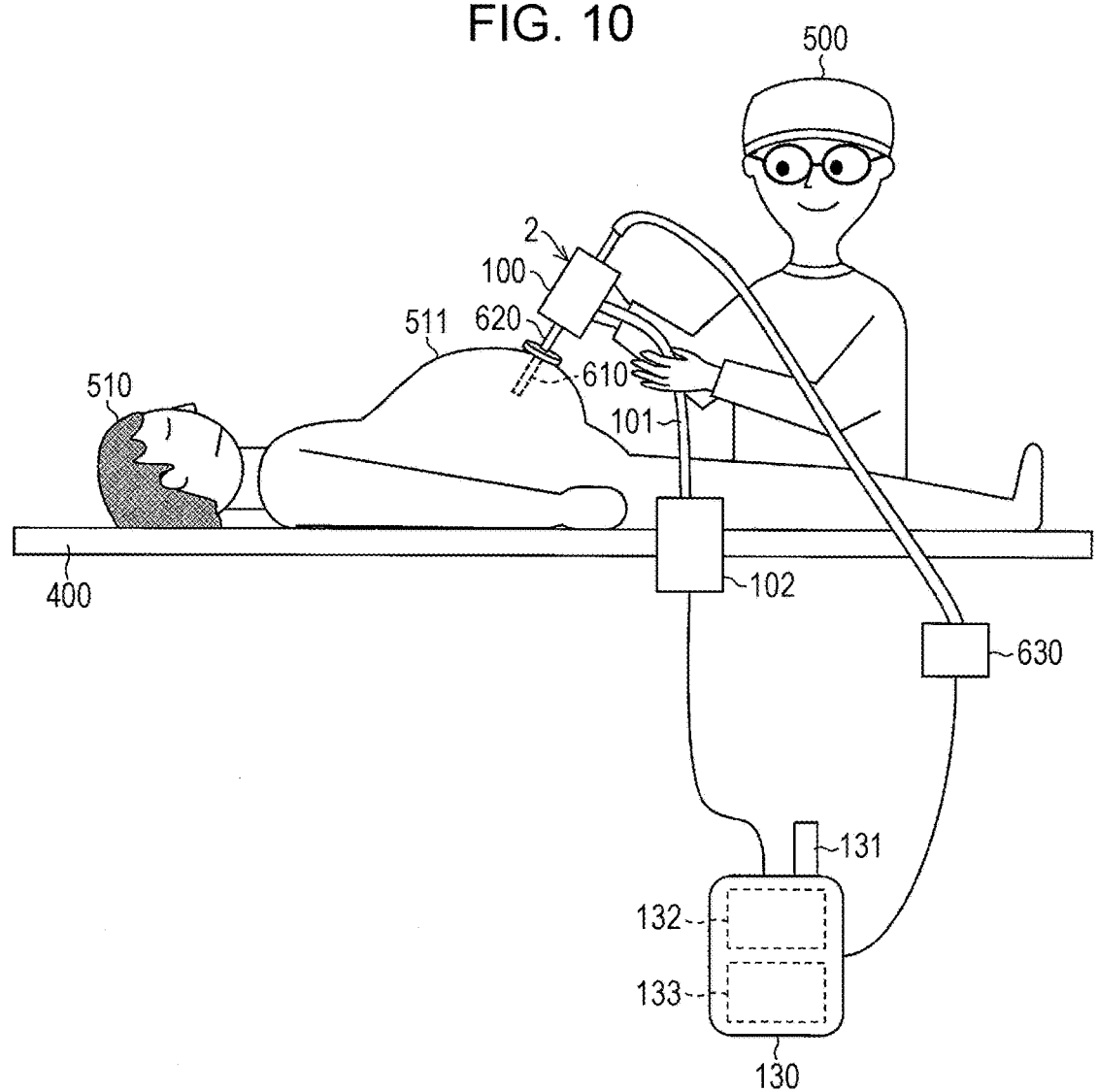
FIG. 10 is a schematic diagram illustrating a schematic configuration of a medical device according to another embodiment of the present invention.

FIG. 10 is a schematic diagram illustrating a schematic configuration of a medical device 2 according to the present embodiment.

As illustrated in FIG. 10, the medical device 2 according to the present embodiment is different from the medical device 1 according to Embodiment 1 in that a pneumatic bending actuator 610 is used as the medical instrument, and in that there is provided an air pump (bending drive device) 630 for bending the pneumatic bending actuator 610. The medical device 2 according to the present embodiment is different from the medical device 1 according to Embodiment 1 in that the controller unit 130 gives an operation instruction to not only the ultrasonic actuator but also the air pump 630.

(Configuration of Insertion Unit)

Figure 11:
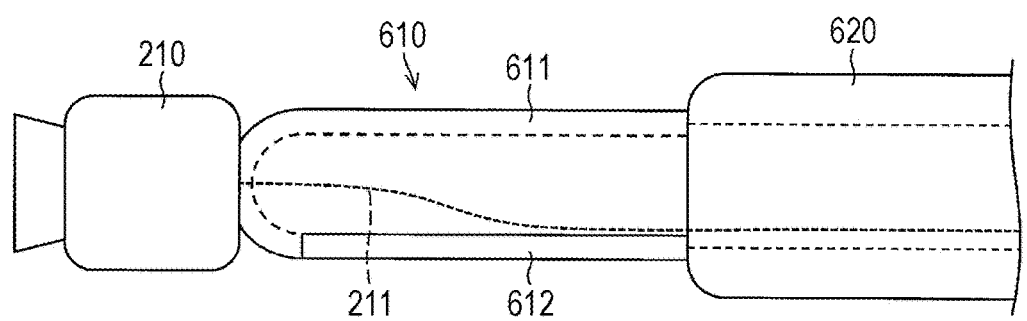
FIG. 11 is a side view illustrating a configuration of a pneumatic bending actuator of the medical device.
Figure 12:
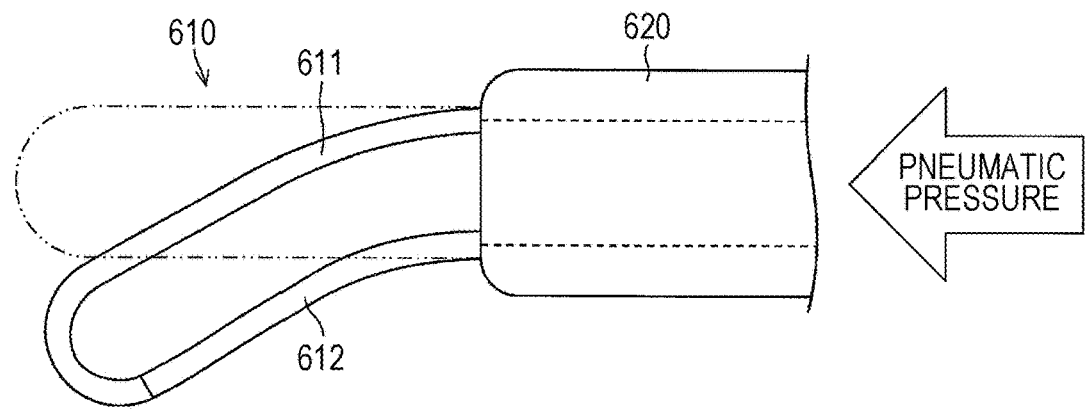
FIG. 12 is a side view illustrating a configuration of the pneumatic bending actuator of the medical device.

As illustrated in FIG. 11, the pneumatic bending actuator 610 according to the present embodiment includes an expandable tube 611 having a hollow and cylindrical shape, a camera 210, and a pipe 620 serving as the insertion unit.

The camera 210 is fixed to an end of the tube 611. The hollow and cylindrical-shaped pipe 620 is connected to and communicates with the other end of the tube 611. The tube 611 is a resilient member, but a partial wall surface (lower side in FIG. 11) of the tube 611 has non-elastic portion 612 whose rigidity is stronger than that of the other wall surface. For example, as a material of the tube 611, silicone is used.

The camera 210 transmits an image in the vicinity of a surgical site which is captured by a video output device (not illustrated), via a signal line 211 passing through the tube 611.

As a material of the pipe 620, a rigid material, for example, an acrylic resin is used so that the pipe 620 is not bent even if air is supplied thereto. Since the signal line 211 passes through the hollow portion, the pipe 620 has a role as not only an air supply passage but also a signal line accommodation housing.

Elasticity of the non-elastic portion 612 may be lower than that of other portions of the tube 611. The elasticity may be set such an extent that the tube 611 expands on the opposite side to the non-elastic portion 612 and the tube 611 does not expand on the non-elastic portion 612 side.

For example, as a material of the non-elastic portion 612, a non-elastic yarn such as a glass fiber or a polyamide fiber may be used, or silicone which is the same material as that of the tube 611 may be used.

(Bending Principle of Tube)

The tube 611 receives air supply from the air pump 630 via the pipe 620. In response to an increase in the air pressure, the opposite side to the non-elastic portion 612 side of the tube 611 expands. On the other hand, the non-elastic portion 612 side does not expand. Accordingly, as illustrated in FIG. 12, the tube 611 is bent to the non-elastic portion 612 side.

Advantageous Effect

As described above, according to the present embodiment, the camera 210 enables ensured visibility in a bending direction of the tube 611 in addition to the axial direction of the pipe 620 (insertion unit) and the rotation direction around the axis.

Therefore, the surgeon 500 can observe the surgical site inside the body lumen in more directions. Accordingly, the surgeon 500 can select the more preferable angle when observing the surgical site.

Modification Example

In the present embodiment, a case where the non-elastic portion 612 is disposed in the main body of the tube 611 has been described as an example. However, without being limited to the present embodiment, the non-elastic portion 612 may be shared with the signal line 211. Furthermore, the signal line 211 shared with the non-elastic portion 612 may be fixed to the outer side of the tube 611 instead of the inner side of the tube 611.

Embodiment 3

Further another embodiment according to the present invention will be described as follows with reference to FIG. 13. In order to facilitate the description, the same reference numerals will be given to members having the same function as the members described in Embodiments 1 and 2, and description thereof will be omitted.

(Overview of Medical Device)

Figure 13:
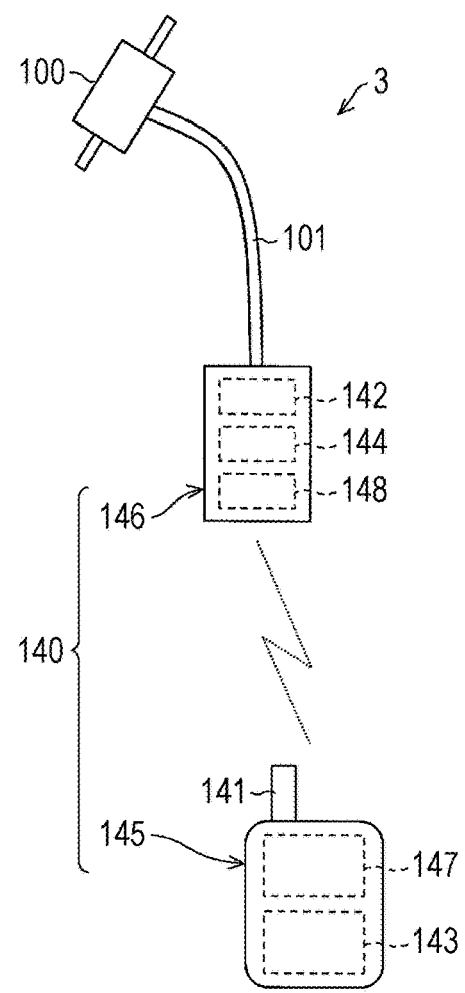
FIG. 13 is a schematic diagram illustrating a schematic configuration of a medical device according to further another embodiment of the present invention.

FIG. 13 is a schematic diagram illustrating a schematic configuration of a medical device 3 according to the present embodiment.

As illustrated in FIG. 13, the medical device 3 according to the present embodiment is different from the medical device according to Embodiments 1 and 2 in that the controller unit is a radio controller unit 140.

(Configuration of Radio Controller)

As illustrated in FIG. 13, the radio controller unit 140 includes a unit main body 145 and an operation instruction unit 146.

The unit main body 145 includes an instruction input unit 141, a transmitter 147 which transmits a signal corresponding to an operation amount in longitudinal and lateral directions of the instruction input unit 141, and a first battery (electric cell) 143 which supplies power to both of these.

The operation instruction unit 146 includes a receiver 148, an operation instruction unit 142, and a second battery (electric cell) 144. The receiver 148 receives the signal transmitted from the transmitter 147. The operation instruction unit 142 generates a drive signal in accordance with the signal received by the receiver 148, and supplies the drive signal to the insertion unit conveyance unit 100. The second battery 144 supplies power to the receiver 148 and the operation instruction unit 142.

The operation instruction unit 146 is installed in (fixed to) the operating table 400, and an end of the flexible arm 101 is fixed to an upper end surface of the operation instruction unit 146. That is, the operation instruction unit 146 also functions as the stand (actuator fixing unit) 102 according to Embodiments 1 and 2.

In accordance with an operation of the instruction input unit 141 which is performed by an operator (not illustrated), the operation instruction unit 142 generates a drive signal corresponding to the alternating voltage, and transmits the drive signal to the upper electrode and the lower electrode. In this manner, an operation instruction can be transmitted to the ultrasonic actuator 110 by means of radio communication.

In the radio controller unit 140, in some cases, an obstacle such as the surgeon 500 may be interposed between the unit main body 145 and the operation instruction unit 146. A radio communication wave needs to have a band which can be freely used by an operator without any license. In a viewpoint of power consumption, it is desirable to use Bluetooth (BT: registered trademark) in which radio communication means can be utilized even if there is an obstacle between radio communication devices, in which a radio wave having the band which can be freely used without any license is used, and in which low power consumption is required.

Advantageous Effect

As described above, according to the present embodiment, the operation instruction is transmitted to the ultrasonic actuator by means of the radio communication. Accordingly, it is possible to more widely secure a working space for the surgeon 500. Therefore, the surgeon 500 can more smoothly perform medical treatment.

As a matter of course, the above-described advantageous effect can also be achieved in a case of employing any medical instrument (insertion unit) according to Embodiments 1 and 2.

Modification Example

According to the present embodiment, a signal input from an operation unit such as the instruction input unit 141 is directly transmitted to the operation instruction unit 146 by the unit main body 145. However, an essential point of the medical device 3 according to the present embodiment is that information provided for the instruction input unit 141 by an operator is reflected in the operation of the ultrasonic actuator by means of the radio communication. Therefore, as long as a configuration realizes this essential point, a form of the radio communication does not matter.

Embodiment 4

Further another embodiment according to the present invention will be described as follows with reference to FIG. 14. In order to facilitate the description, the same reference numerals will be given to members having the same function as the members described in Embodiments 1 to 3, and description thereof will be omitted.

Figure 14:
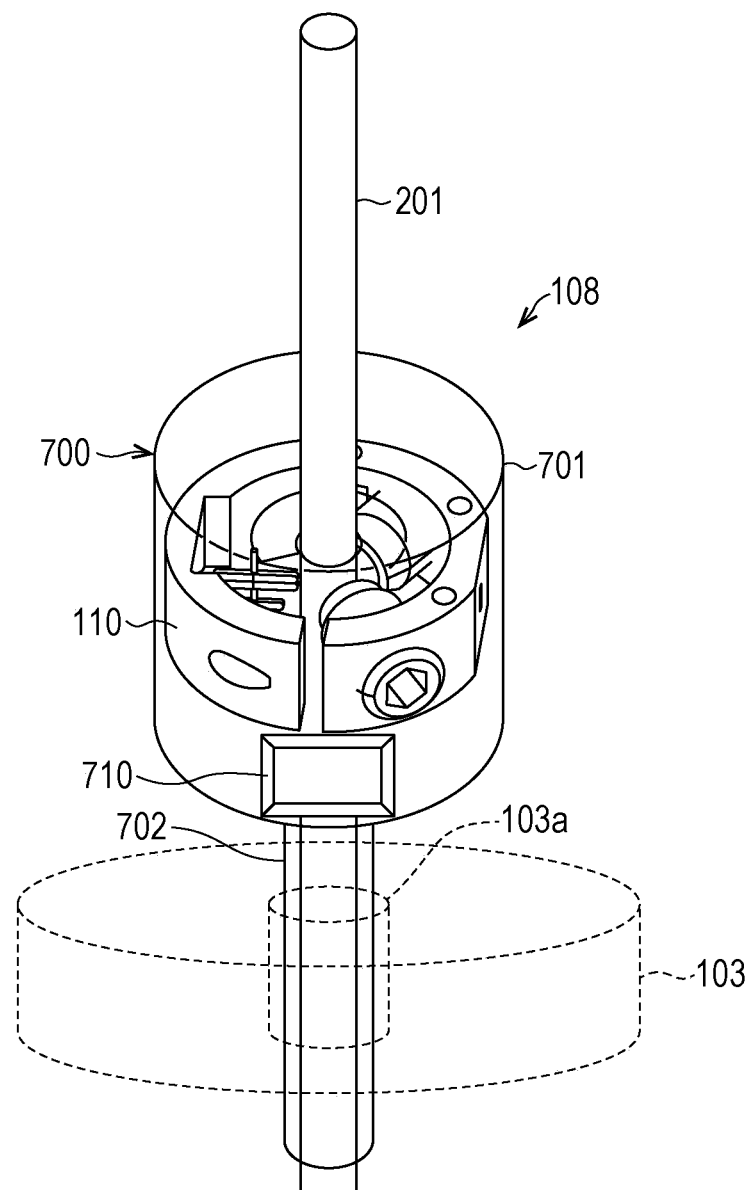
FIG. 14 is a schematic diagram illustrating a schematic configuration of an insertion unit conveyance unit according to further another embodiment of the present invention.

FIG. 14 is a schematic diagram illustrating a schematic configuration of an insertion unit conveyance unit 107 according to the present embodiment. As illustrated in FIG. 14, the insertion unit conveyance unit 107 according to the present embodiment is different from the insertion unit conveyance unit 100 according to Embodiments 1 to 3 in that a trocar 700 is used as the actuator holding unit 109.

(Configuration of Trocar)

The trocar 700 is a medical instrument for inserting a surgical instrument into a body lumen of a patient, and is generally used in surgery using the rigid endoscope. As illustrated in FIG. 14, the trocar 700 includes a cylindrical trocar housing 701 and a hollow needle 702.

The trocar housing 701 is a hollow housing which secures an enough space in which the ultrasonic actuator 110 can be internally incorporated. The trocar housing 701 holds the ultrasonic actuator 110.

The needle 702 is a cylindrical member having an enough hollow portion through which the insertion unit 201 of the rigid endoscope can penetrate. The outer diameter is smaller than the diameter of a through-hole 103a of the surgical port 103. An end of the needle 702 is connected to and communicates with an end of the trocar housing 701. The needle 702 is inserted into the surgical port 103 from the through-hole 103a. In this manner, the needle 702 is fixed to the surgical port 103. The medical device 3 may separately include a fixing portion for fixing the trocar 700 to the surgical port 103. For example, a corresponding engagement portion may be disposed in the trocar 700 and the surgical port 103.

Here, an external terminal 710 is installed on a side surface of the trocar housing 701. The controller unit and the insertion unit conveyance unit 107 are electrically connected to each other through the external terminal 710.

The trocar 700 can employ those which are generally used in the medical field, as long as the trocar housing 701 secures an enough space in which the ultrasonic actuator 110 can be incorporated.

Advantageous Effect

As described above, according to the present embodiment, the trocar 700 is fixed to the surgical port 103, thereby fixing the ultrasonic actuator 110 incorporated in the trocar housing 701 to a surgical site. Therefore, it is not necessary to use the flexible arm 101 and the stand 102. Accordingly, it is possible to more widely secure a working space for the surgeon 500. Therefore, the surgeon 500 can more smoothly perform medical treatment.

As a matter of course, the above-described advantageous effect can also be achieved in a case of employing any medical instrument (insertion unit) according to Embodiments 1 and 2.

Modification Example

An important characteristic of the insertion unit conveyance unit 107 according to the present embodiment is that the ultrasonic actuator 110 is fixed to the trocar 700 arranged in the vicinity of a surgical site. Therefore, for example, the ultrasonic actuator 110 does not need to be incorporated in the trocar housing 701. A configuration may be adopted in which the ultrasonic actuator 110 is installed in an end of the trocar housing 701.

It is not always necessary to use the surgical port 103, and the surgical port 103 can be omitted.

Embodiment 5

Further another embodiment according to the present invention will be described as follows with reference to FIG. 15. In order to facilitate the description, the same reference numerals will be given to members having the same function as the members described in Embodiments 1 to 4, and description thereof will be omitted.

Figure 15:
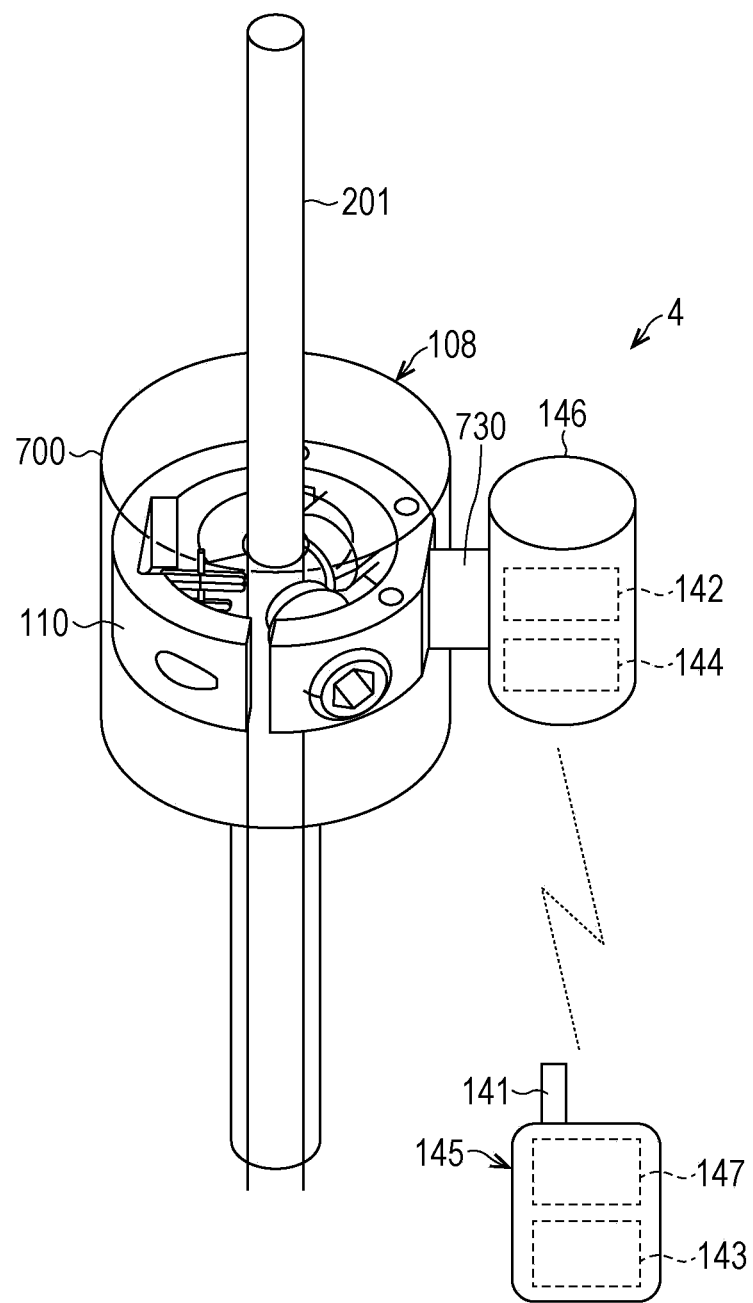
FIG. 15 is a schematic diagram illustrating a schematic configuration of a medical device according to further another embodiment of the present invention.

FIG. 15 is a schematic diagram illustrating a schematic configuration of a medical device 4 according to the present embodiment. The medical device 4 includes the unit main body 145 and the operation instruction unit 146. As illustrated in FIG. 15, an insertion unit conveyance unit 108 according to the present embodiment is different from the insertion unit conveyance unit 107 according to Embodiment 4 in that the operation instruction unit 146 is connected to a side surface of the trocar housing 701 by a connector 730 disposed on a side surface of the operation instruction unit 146.

The operation instruction unit 146 drives the ultrasonic actuator 110 included in the trocar 700, based on the instruction received from the unit main body 145 of the radio controller unit by means of the radio communication.

The connector 730 and the operation instruction unit 146 are attachable to and detachable from the trocar 700.

Advantageous Effect

As described above, according to the present embodiment, it is possible to detach the operation instruction unit 146 for mounting a semiconductor component which is vulnerable to a high temperature. Therefore, the trocar 700 alone can be subjected to sterilization treatment, particularly, sterilization treatment using the high temperature, such as autoclave sterilization (high pressure steam sterilization). Therefore, it is possible to more reliably sterilize and clean the trocar 700.

It is unnecessary to consider heat resistance for the operation instruction unit 146. Accordingly, a general semiconductor component can be used, and thus, it is possible to manufacture the operation instruction unit 146 at low cost.

The operation instruction is transmitted to the ultrasonic actuator 110 by means of the radio communication. Therefore, the present embodiment can also obtain the same advantageous effect as that according to Embodiment 3.

CONCLUSION

According to Aspect 1 of the present invention, there is provided the medical device (1 to 4) which adjust a position of the medical instrument (rigid endoscope 200) including the rod-like insertion unit (201) for inserting the medical instrument into the body. The medical device includes the actuator (ultrasonic actuator 110 and pneumatic bending actuator 610) that holds the insertion unit of the medical instrument, and that displaces or rotates the insertion unit with respect to the actuator, and the actuator fixing unit (for example, the flexible arm 101, the stand 102, the actuator holding unit 109, the operation instruction unit 146 which also serves as the stand, or the trocar 700) that fixes the position of the actuator.

According to the above-described configuration, the actuator holding the insertion unit of the medical instrument is fixed to a surgical site. Accordingly, it is possible to provide the medical device whose occupied space is reduced. According to the above-described configuration, compared to the medical robot system using the surgical robot, it is possible to manufacture the medical device at low cost.

In the medical device according to Aspect 2 of the present invention, in Aspect 1 described above, the actuator fixing unit may be configured to include the trocar (700).

According to the above-described configuration, it is not necessary to use the flexible arm the stand. Accordingly, it is possible to more widely secure a working space for an operator. Therefore, the operator can more smoothly perform medical treatment.

In the medical device according to Aspect 3 of the present invention, in Aspect 1 or 2 described above, the above-described actuator may be configured to displace the insertion unit in the axial direction of the insertion unit (201).

According to the above-described configuration, while the medical device whose occupied space is reduced is realized, the medical instrument can have suitable access to a surgical site in the axial direction of the insertion unit.

In the medical device according to Aspect 4 of the present invention, in any one of Aspects 1 to 3 described above, the actuator may be configured to rotate the insertion unit by using the rod-like insertion unit as the rotation axis.

According to the above-described configuration, while the medical device whose occupied space is reduced is realized, the medical instrument can have suitable access to a surgical site in the rotation direction of the insertion unit which uses the insertion unit itself as the rotation axis.

In the medical device according to Aspect 5 of the present invention, in any one of Aspects 1 to 4 described above, a configuration may be adopted which includes the bending drive device (air pump 630) for bending the insertion unit.

According to the above-described configuration, while the medical device whose occupied space is reduced is realized, the medical instrument can have suitable access to a surgical site in the bending direction of the tube configuring the insertion unit.

In the medical device according to Aspect 6 of the present invention, in any one of Aspects 1 to 5 described above, the actuator may be configured to include the friction drive element (ultrasonic vibrator 114) which displaces or rotates the insertion unit by using the friction with the surface of the insertion unit.

According to the above-described configuration, compared to the actuator which does not include the friction drive element, it is possible to minimize the contact area between the actuator and the insertion unit. Therefore, it is possible to reduce a possibility that the actuator may be poorly operated in a case where liquids such as blood and contaminants enter the contact portion between the actuator and the insertion unit.

According to the above-described configuration, compared to the actuator which does not include the friction drive element, it is possible to minimize the friction force generated in the contact portion between the actuator and the insertion unit, when the medical instrument is detached therefrom. Therefore, it is possible to easily replace and clean the medical instrument.

In the medical device according to Aspect 7 of the present invention, in Aspect 6 described above, the friction drive element may be a single element which can selectively displace or rotate the insertion unit with respect to the actuator.

According to the above-described configuration, the single friction drive element selectively displaces or rotates the insertion unit. Therefore, compared to the actuator which realizes the conveyance in a certain direction by using multiple friction drive elements, it is possible to further reduce a possibility that the actuator is poorly operated due to dirt adhering to the insertion unit.

According to the above-described configuration, compared to the actuator which includes the multiple friction drive elements, it is possible to simplify a structure of the actuator. Therefore, the actuator can be miniaturized, and thus, it is possible to provide the medical device whose occupied space is reduced. It is possible to easily manufacture the medical device at low cost.

In the medical device according to Aspect 8 of the present invention, in Aspect 6 or 7 described above, the friction drive element may be configured to displace or rotate the insertion unit by using the standing wave vibration.

According to the above-described configuration, a stable vibration (standing wave vibration) whose amplitude is large can be generated in the friction drive element. Therefore, it is possible to reduce a possibility that the actuator may be poorly operated in a case where liquids such as blood and contaminants enter the contact portion between the actuator and the insertion unit.

In the medical device according to Aspect 9 of the present invention, in any one of Aspects 6 to 8 described above, the friction drive element may be configured to include the ultrasonic vibrator (114).

According to the above-described configuration, the ultrasonic vibrator employs major components including the vibrator, the piezoelectric element such as piezoelectric ceramics, and the electrode, does not employ a coil. Therefore, it is possible to simplify a structure of the friction drive element, thereby contributing to the miniaturized actuator.

According to the above-described configuration, a very strong force can be intermittently applied to the contact surface between the piezoelectric element and the vibrator. Therefore, it is possible to excite a sufficient vibration to convey the insertion unit by using little power.

In any one of Aspects 1 to 9 described above, the medical device according to Aspect 10 of the present invention may further include the instruction input unit (131, 141) that receives an instruction from a user, and the control device (controller unit 130) that includes the operation instruction unit (132, 142) which gives an operation instruction to the actuator. The actuator fixing unit and the control device may be configured so that both of these are detachably connected to each other by the cable.

According to the above-described configuration, the actuator fixing unit and the control device are connected to each other by the cable. Accordingly, the control device can be located at a position away from the operating table by selecting the length of the cable. Therefore, it is possible to more widely secure a working space for an operator.

According to the above-described configuration, only the actuator fixing unit having no semiconductor component which is vulnerable to heat can be individually subjected to sterilization treatment. Therefore, it is possible to perform the sterilization treatment on the actuator fixing unit at a high temperature which ensures a high sterilization effect.

In any one of Aspects 1 to 9 described above, the medical device according to Aspect 11 of the present invention may further include the instruction input unit that receives an instruction from a user, and the control device including the operation instruction unit (radio controller unit 140) which gives an operation instruction to the actuator in accordance with the above-described instruction. The operation instruction unit may be configured to give the operation instruction to the actuator by means of radio communication.

According to the above-described configuration, it is unnecessary to provide a cable for connecting the actuator fixing unit and the control device to each other. Accordingly, it is possible to more widely secure a working space for an operator by arranging the control device at a position away from the operating table.

In the medical device according to Aspect 12 of the present invention, in any one of Aspects 1 to 11 described above, the actuator fixing unit may be configured so that the electric cell (first battery 143) for driving the actuator is incorporated therein.

According to the above-described configuration, it is possible to reduce the wires connected to the actuator fixing unit. Accordingly, it is possible to secure a working space for an operator. Therefore, it is possible to more widely secure the working space for the operator.

In the medical device according to Aspect 13 of the present invention, in any one of Aspects 1 to 12 described above, the actuator fixing unit may be configured to include the flexible arm the stand (flexible arm 101 and stand 102) which supports the actuator so as to fix the position of the actuator.

According to the above-described configuration, the actuator holding the insertion unit of the medical instrument is fixed by the small-sized flexible arm the stand. Accordingly, it is possible to provide the medical device whose occupied space is reduced. According to the above-described configuration, the flexible arm is easily transformable by a human hand's force. Accordingly, it is possible to conveniently fix the actuator at an operator's desired position. According to the above-described configuration, compared to the medical robot system using the surgical robot, it is possible to manufacture the medical device at low cost.

In the medical device according to Aspect 14 of the present invention, in Aspect 2 described above, a configuration may be adopted which includes the fixing portion for fixing the actuator to the surgical port.

According to the above-described configuration, the fixing portion can fix the position of the actuator to a surgical site. Therefore, it is possible to more widely secure a working space for an operator.

In the medical device according to Aspect 15 of the present invention, in any one of Aspects 1 to 14 described above, the actuator may be configured to displace or rotate the insertion unit of the endoscope (rigid endoscope 200) serving as the medical instrument.

According to the above-described configuration, while the medical device whose occupied space is reduced is realized, it is possible to suitably ensure visibility for operator's work.

The present invention is not limited to the above-described respective embodiments, and can be modified in various ways within the scope of claims. The technical scope of the present invention also includes embodiments obtained by properly combining technical means respectively disclosed in the different embodiments. A new technical characteristic may be formed by combining the technical means respectively disclosed in each embodiment.

INDUSTRIAL APPLICABILITY

The present invention can be utilized for a medical device, and in particular, the present invention can be preferably utilized for a medical device including an endoscopic camera, manipulator, and forceps for the celoscope surgery.

REFERENCE SIGNS LIST

1 TO 4 MEDICAL DEVICE
40 VIBRATOR
41 TO 44 PIEZOELECTRIC ELEMENT (VIBRATION GENERATION ELEMENT)
41a TO 44a UPPER ELECTRODE (VIBRATION GENERATION ELEMENT)
41b TO 44b LOWER ELECTRODE (VIBRATION GENERATION ELEMENT)
45 PROJECTION
46 NARROW PORTION
48 KEY
100, 107, 108 INSERTION UNIT CONVEYANCE UNIT
101 FLEXIBLE ARM (ACTUATOR FIXING UNIT)
102 STAND (ACTUATOR FIXING UNIT)
103 SURGICAL PORT
109 ACTUATOR HOLDING UNIT (ACTUATOR FIXING UNIT)
110 ULTRASONIC ACTUATOR (ACTUATOR, FRICTION DRIVE ACTUATOR)
111, 112 HOUSING (FIRST HOUSING, SECOND HOUSING)
113 STAY (HOLDING UNIT)
114 ULTRASONIC VIBRATOR (FRICTION DRIVE ELEMENT)
115 BALL BEARING (SLIDING BODY)
116 PRELOADING SPRING (RESTORING MEMBER)
130 CONTROLLER UNIT (CONTROL DEVICE)
131, 141 INSTRUCTION INPUT UNIT
132 DRIVE SIGNAL GENERATION UNIT (VOLTAGE SUPPLY UNIT, OPERATION INSTRUCTION UNIT)
133, 143, 144 BATTERY (ELECTRIC CELL)
140 RADIO CONTROLLER UNIT (CONTROL DEVICE)
142 OPERATION INSTRUCTION UNIT
145 UNIT MAIN BODY
146 OPERATION INSTRUCTION UNIT (ACTUATOR FIXING UNIT)
147 TRANSMITTER
148 RECEIVER
200 RIGID ENDOSCOPE
201 INSERTION UNIT (OPERATION ELEMENT)
610 PNEUMATIC BENDING ACTUATOR
620 PIPE (INSERTION UNIT, OPERATION ELEMENT)
630 AIR PUMP (BENDING DRIVE DEVICE)
700 TROCAR (ACTUATOR FIXING UNIT)

The invention claimed is:

1. A medical device which adjusts a position of a medical instrument with respect to a human body, the medical instrument including a rod that inserts the medical instrument into the human body, the medical device comprising:
   an actuator that holds the rod of the medical instrument, and that displaces or rotates the rod relative to the actuator; and
   a hollow housing that fixes a position of the actuator to a surgical site, wherein
   the actuator includes a first housing and a second housing;
   the first housing and the second housing are separate elements that are connected to one another by a spring so as to be openable and closeable;
   the spring applies a restoring force in a direction that closes together the first housing and the second housing;
   the actuator holds the rod at respective contact points on the first and second housings;
   the actuator includes a friction driver that displaces or rotates the rod by using friction with a surface of the rod; and
   the friction driver displaces or rotates the rod by applying a standing wave vibration to the rod.

2. The medical device according to claim 1,
   wherein at least one of the contact points is a driving point to displace or rotate the rod by using friction with a surface of the rod.

3. The medical device according to claim 1,
   wherein at least one of the contact points is a multi-degree-of-freedom driving point to displace or rotate the rod by using friction with a surface of the rod.

4. The medical device according to claim 1,
wherein the hollow housing is a trocar.

5. The medical device according to claim 4, further comprising:
a needle which fixes the hollow housing to a surgical port.

6. The medical device according to claim 1,
wherein the actuator displaces the rod in an axial direction thereof.

7. The medical device according to claim 1,
wherein the actuator rotates the rod around a rotation axis thereof.

8. The medical device according to claim 1, further comprising:
a bending drive device that bends the rod.

9. The medical device according to claim 1,
wherein the friction driver is a single device which can selectively displace or rotate the rod relative to the actuator.

10. The medical device according to claim 1,
wherein the friction driver is an ultrasonic vibrator.

11. The medical device according to claim 1, further comprising:
a controller that receives an instruction from a user and gives an operation instruction to the actuator in accordance with the instruction,
wherein the hollow housing and the controller are detachably connected to each other by a cable.

12. The medical device according to claim 1, further comprising:
a controller receives an instruction from a user and gives an operation instruction to the actuator in accordance with the instruction,
wherein the controller gives the operation instruction to the actuator through radio communication.

13. The medical device according to claim 1,
wherein the hollow housing has an incorporated electric cell for driving the actuator.

14. The medical device according to claim 1,
wherein the hollow housing is provided with a flexible arm stand which supports the actuator so as to fix the position of the actuator.

15. The medical device according to claim 1,
wherein the actuator displaces or rotates the rod of an endoscope serving as the medical instrument.

* * * * *